US009421017B2

(12) United States Patent
Seguin

(10) Patent No.: US 9,421,017 B2
(45) Date of Patent: Aug. 23, 2016

(54) METHODS AND APPARATUS USING BRANCHED BALLOON FOR TREATING PULMONARY ARTERIAL HYPERTENSION

(71) Applicant: Jacques Seguin, Launen bei Gstaad (CH)

(72) Inventor: Jacques Seguin, Launen bei Gstaad (CH)

( * ) Notice: Subject to any disclaimer, the term of this patent is extended or adjusted under 35 U.S.C. 154(b) by 0 days.

(21) Appl. No.: 14/594,012

(22) Filed: Jan. 9, 2015

(65) Prior Publication Data

US 2015/0196303 A1 Jul. 16, 2015

Related U.S. Application Data

(63) Continuation of application No. PCT/IB2015/050066, filed on Jan. 5, 2015.

(30) Foreign Application Priority Data

Jan. 15, 2014 (FR) ...................................... 14 50326

(51) Int. Cl.
  *A61B 17/12* (2006.01)
  *A61M 25/10* (2013.01)
  *A61M 25/00* (2006.01)

(52) U.S. Cl.
  CPC ... *A61B 17/12136* (2013.01); *A61B 17/12036* (2013.01); *A61B 17/12109* (2013.01);
  (Continued)

(58) Field of Classification Search
  CPC .................. A61B 17/12022; A61B 17/12031; A61B 17/12036; A61B 17/1204; A61B 17/12099; A61B 17/12109; A61B 17/12122; A61B 17/12131; A61B 17/12136; A61B 2017/1205; A61M 25/10; A61M 25/1002; A61M 25/1011; A61M 25/10182; A61M 25/1025; A61M 25/104; A61M 2025/1015; A61M 2025/1045
  See application file for complete search history.

(56) References Cited

U.S. PATENT DOCUMENTS

| 4,902,273 A | 2/1990 | Choy et al. |
| 5,112,303 A | 5/1992 | Pudenz et al. |

(Continued)

FOREIGN PATENT DOCUMENTS

| CN | 102657910 A | 9/2012 |
| DE | 19508129 A1 | 9/1996 |

(Continued)

OTHER PUBLICATIONS

International search report and written opinion dated Mar. 24, 2015 for PCT/IB2015/050066.

(Continued)

*Primary Examiner* — Ryan J Severson
(74) *Attorney, Agent, or Firm* — Wilson Sonsini Goodrich & Rosati

(57) ABSTRACT

A device for treating pulmonary hypertension includes an inflatable balloon structure (1), an implantable port (9), and a conduit (2) connecting the balloon (1) and the implantable port in a sealed manner. The balloon, the port and the conduit are filled with a gas, and the pressure is such that the balloon (1) is normally inflated but is capable of being compressed during systole. The inflatable balloon (1) has first and second segments sized to extend into the left branch and the right branch of the pulmonary artery bifurcation respectively. The conduit (2) may connected in a T-junction to a middle portion of the balloon (1) or may be bifurcated into first and second branches (12*a*,12*b*) which are connected to the first and second balloon segments (13*a*,13*b*), respectively. The device may also have guide tubes opening at the longitudinal ends of the balloon (1) and guide wires (4, 6) engaged and capable of sliding in said guide tubes.

12 Claims, 5 Drawing Sheets

(52) U.S. Cl.
CPC ...... *A61M25/0071* (2013.01); *A61M 25/1011* (2013.01); *A61B 2017/1205* (2013.01); *A61M 25/1002* (2013.01); *A61M 2025/1045* (2013.01); *A61M 2025/1052* (2013.01); *A61M 2025/1061* (2013.01); *A61M 2025/1093* (2013.01)

(56) References Cited

U.S. PATENT DOCUMENTS

| | | | |
|---|---|---|---|
| 5,833,655 A | 11/1998 | Freed et al. | |
| 6,013,054 A * | 1/2000 | Jiun Yan | A61M 25/1029 604/103.07 |
| 6,017,324 A | 1/2000 | Tu et al. | |
| 6,053,891 A | 4/2000 | Decampli | |
| 6,558,349 B1 | 5/2003 | Kirkman | |
| 6,576,007 B2 † | 6/2003 | Dehdashtian | |
| 6,579,224 B1 | 6/2003 | Burton et al. | |
| 7,468,050 B1 | 12/2008 | Kantrowitz | |
| 8,876,850 B1 | 11/2014 | Vollmers et al. | |
| 2004/0093007 A1 | 5/2004 | Sussman et al. | |
| 2006/0129083 A1 | 6/2006 | Brenneman et al. | |
| 2006/0241745 A1 | 10/2006 | Solem | |
| 2010/0094247 A1* | 4/2010 | Kaluski | A61F 2/954 604/500 |
| 2013/0245665 A1 | 9/2013 | Scandurra et al. | |
| 2015/0216531 A1 | 8/2015 | Seguin | |

FOREIGN PATENT DOCUMENTS

| | | |
|---|---|---|
| DE | 102005060197 A1 | 6/2007 |
| EP | 0366814 A1 | 5/1990 |
| WO | WO 90/06086 A1 | 6/1990 |
| WO | WO 96/12518 A1 | 5/1996 |
| WO | WO 93/17731 A1 | 9/1996 |
| WO | WO 96/34647 A1 | 11/1996 |
| WO | WO 98/50100 A1 | 11/1998 |
| WO | WO 00/66030 A1 | 11/2000 |
| WO | WO 2012/071395 A1 * | 5/2012 |
| WO | WO 2013/185138 A1 | 12/2013 |

OTHER PUBLICATIONS

International search report and written opinion dated Mar. 24, 2015 for PCT/IB2015/050068.
Office action dated Sep. 28, 2015 for U.S. Appl. No. 14/594,021.
Office action dated Feb. 17, 2016 for U.S. Appl. No. 14/594,021.

\* cited by examiner
† cited by third party

METHODS AND APPARATUS USING BRANCHED BALLOON FOR TREATING PULMONARY ARTERIAL HYPERTENSION

CROSS-REFERENCE TO RELATED APPLICATIONS

This application is a continuation of International Patent Application No. PCT/IB2015/050066, filed Jan. 5, 2015, which claims priority to FR Patent Application No. 1450326 (1000224026), filed Jan. 15, 2014, the contents of which are incorporated herein by reference.

BACKGROUND OF THE INVENTION

1. Field of the Invention

The present invention relates generally to medical devices and methods. More particularly, the present invention relates to a device for the treatment of pulmonary arterial hypertension.

Pulmonary arterial hypertension is a disease that affects a large number of people, either directly through pulmonary fibrosis or indirectly as a result of respiratory failure or left ventricular failure. Pulmonary arterial hypertension usually results from an increase in peripheral pulmonary vascular resistance and a decrease in pulmonary arterial compliance.

One approach for treating pulmonary hypertension relies on placing a balloon in the trunk of the pulmonary artery, or two balloons in the branches of the pulmonary artery bifurcation. The balloon(s) are connected to an implantable port and are normally inflated with a gas to partially extend across the trunk or the branches. The port will hold excess gas that provides a "gas reserve." The balloon(s) are fully expanded during right ventricular diastole, and thus will limit the backflow of blood. During right ventricular systole, however, the balloons compress in response to the increased blood pressure so that they do no significantly impede the flow of blood into the pulmonary artery. Such compression temporarily generates an overpressure which is mitigated by the excess volume provided by the implantable port as well as by the conduit connecting the port to the balloon.

While quite effective for treating pulmonary hypertension, the placement of these balloons in the trunk or the branches of the pulmonary artery can be difficult. In particular, with present balloon designs and placement protocols, the balloons may become displaced during systole or diastole, and such displacement can reduce device efficiency and in some cases cause vascular trauma. Moreover, the present devices can be difficult to remove and replace if they become leak or otherwise become dysfunctional over time.

For these reasons, it would be desirable to provide improved pulmonary artery balloon catheter designs and placement protocols which minimize the risks associated with balloon mobility. The balloon designs should also be amenable to replacement should that become necessary. The present invention will meet at least some of these objectives.

2. Description of the Background Art

Pulmonary arterial catheters and other devices are described in U.S. Pat. Nos. 4,902,273; 6,017,324; 6,053,891; and 8,876,850; and PCT Applications WO1993/17731 and 2013/185138.

SUMMARY OF THE INVENTION

In a first aspect, the present invention provides a system for treating pulmonary hypertension. The system comprises an implantable port configured for subcutaneous implantation and having an internal chamber. A guide conduit structure is attached at one end thereof to the implantable port, and an inflatable balloon structure is attached to another end of the guide conduit. The inflatable balloon structure includes a first lateral balloon segment or a first balloon and a second lateral balloon segment or a second balloon, and the balloon structure is configured so that when the guide conduit is positioned in a pulmonary artery, the first balloon segment or the first balloon will occupy a left branch of the pulmonary artery and the second balloon segment or the second balloon will occupy a right branch of the pulmonary artery. The implantable port provides needle access to inflate the balloon segments or balloons and also acts as a chamber or reservoir to temporarily accommodate "excess" gas which results from the higher pressure during systole when in comparison to diastole. Such design provides the therapeutic benefits associated with conventional pulmonary artery balloons while significantly improving balloon stability and reducing the risk of balloon mobility after initial placement. The device and methods of the present invention can be used temporarily, e.g. to treat acute post-operative high pulmonary pressure, or chronically, e.g. to treat chronic high pulmonary pressure after pulmonary embolism or pulmonary fibrosis. In the latter case the balloon catheter can be changed when necessary.

In specific embodiments, the implantable port may be configured to receive a needle which is transcutaneously advanced to deliver a balloon(s) inflation medium. In other embodiments, the balloon structure may include a single balloon structure forming said first lateral balloon segment and said second lateral balloon segment, and the guide conduit may include first and second guide tubes, wherein the first guide tube passes along the first lateral balloon segment to provide a guide wire path along the first lateral balloon segment and the second guide tube passes along the second lateral balloon segment to provide a guide wire path along this second lateral balloon segment.

In some embodiments, a distal end of the guide conduit structure is connected in a T-junction to a central zone of said single balloon, located between said first lateral balloon segment and said second lateral balloon segment. In other embodiments, a distal end of the guide conduit structure is bifurcated into first and second branches with the first balloon attached at a distal end of the first branch and the second balloon attached at a distal end of the second branch.

In other embodiments, the balloon structure may include a single balloon structure forming said first lateral balloon segment and said second lateral balloon segment, and the guide conduit may include first and second guide tubes, wherein the first guide tube passes through the first lateral balloon segment to provide a guide wire path therethrough and the second guide tube passes through the second lateral balloon segment to provide a guide wire path therethrough. In still other embodiments, a sheath may be configured to constrain the inflatable balloon structure for delivery to a base of the pulmonary artery and to allow advancement of the first and second lateral balloon segments or first and second balloons through the pulmonary artery into the left and right branches of the pulmonary artery, respectively. In an exemplary embodiment, the inflatable balloon may be configured so that the first and second lateral segments fold into a side-by-side configuration when constrained by the sheath. In an alternative exemplary embodiment, the inflatable balloon may be configured so that the first and second lateral segments lie along a common axis in parallel to an axis of the guide conduit when constrained by the sheath.

In a second aspect of the present invention, a method for treating pulmonary hypertension comprises advancing at least one balloon catheter through a pulmonary artery so that a first lateral balloon segment or a first balloon enters a left branch of the pulmonary artery and a second lateral balloon segment or a second balloon enters a right branch of the pulmonary artery. A port connected to the balloon catheter by a guide conduit is implanted so that the guide conduit passes through the pulmonary artery. The first and second lateral balloon segments or first and second balloons are filled with a compressible filling medium, typically through the port, so that the balloon segments or balloons will partially occupy the cross-section of the pulmonary artery branches and will partially collapse during systole. Such a delivery protocol significantly improves balloon stability and reduces the risk of balloon mobility after initial placement.

In specific embodiments of the methods, advancing the at least one balloon catheter comprises advancing a single balloon catheter having a single balloon structure including first and second lateral balloon segments attached in a T-junction to a distal end of the single balloon catheter. In other embodiments of the methods, advancing comprises advancing a single balloon catheter having a bifurcated distal end including a first branch attached to the first balloon and a second branch attached to the second balloon. In still other embodiments of the methods, advancing comprises advancing first and a second balloon catheters wherein the first balloon catheter carries the first balloon and the second balloon catheter carries the second balloon.

In particular embodiments, the balloon catheter is advanced up an inferior vena cava, across a tricuspid valve, through the pulmonary valve, and into the pulmonary artery trunk. The first lateral balloon segment and the second lateral balloon segment balloon are typically constrained within a sheath while they are being advanced into the pulmonary artery trunk. The first lateral balloon segment is usually advanced from the sheath over a first guide wire positioned through the pulmonary artery trunk into the left branch of the pulmonary artery, and the second lateral balloon segment is usually advanced over a second guide wire positioned through the pulmonary artery trunk into the right branch of the pulmonary artery. The first and second lateral segments may be folded into a side-by-side configuration within the sheath while they are advanced into the pulmonary artery. Alternatively, the first and second lateral segments may be axially aligned along a common axis in parallel to an axis of the guide conduit while they are advanced into the pulmonary artery.

In more detailed implementations of the present invention, the devices may comprise an inflatable balloon, an implantable port and a conduit connecting the balloon and the implantable port in a sealed manner, this balloon, this port and this conduit being filled with fluid; the pressure of this fluid is such that the balloon is normally inflated but is capable of being compressed, thereby temporarily generating an overpressure in the said implantable port, due to the fluid flowing in the said conduit; the inflatable balloon comprises a middle portion, a first lateral portion extending over a first side of this middle portion and a second lateral portion extending over a second side of this middle portion, opposite the first side;

a. the said inflatable balloon is dimensioned in a manner such that, during the implantation, the said first lateral portion is adapted to be placed in one of the left or right branches of the bifurcation that is formed by the pulmonary artery, and the said second lateral portion is adapted to be placed in the other of these left or right branches;

b. the said conduit is connected to the said middle portion of the balloon; and where the device may further comprises;

c. a first guide tube, extending along the said conduit, then along the said middle portion and along the first lateral portion of the balloon, until it opens out at a first of the longitudinal ends of the balloon, to which the first guide tube is connected;

d. a second guide tube, extending along the said conduit, then along the said middle portion and along the said second lateral portion of the balloon, until it opens out at the second longitudinal end of the balloon, to which this second guide tube is connected;

e. a first guide wire engaged and capable of sliding in the said first guide tube, and f. a second guide wire engaged and capable of sliding in the said second guide tube.

The device may be placed in a tubular sheath forming a routing member for routing the device to the implantation site, this tubular sheath being adapted to house within its interior the balloon in a deflated state, the said conduit and the said guide tubes containing the said guide wires, and being adapted to release this balloon, this conduit and these guide tubes.

In practice, the tubular sheath may be introduced into the right heart, up through the pulmonary valve and into the interior of the trunk of the pulmonary artery, then the guide wires are deployed so as to be extended, and used to introduce the said lateral portions of the balloon into the respective branches of the pulmonary artery. The said conduit extends in the bifurcation and in the trunk of the pulmonary artery, and the assembly formed by the said lateral portions of the balloon and this conduit ensures perfect retention of the balloon within the pulmonary artery, without risk of mobility of this balloon.

Once the balloon is set up in position in this manner, the guide wires may be retracted and the tubular sheath is removed, and then the port is implanted. The fluid is then introduced into this port, and into the said conduit and into the balloon, at the pressure level that enables the appropriate inflation and compression of the balloon.

The device according to the invention, so implanted, allows an increase of the diastolic pressure of the pulmonary artery, a decrease of the systolic pressure of the pulmonary artery, an increase of the arterial compliance and an immediate and sustained increase in cardiac output, without any risk of mobility of the balloon, the latter being held in position by the engagement of its lateral portions in the said left and right branches as well as by the engagement of the said conduit in the trunk of the pulmonary artery.

The guide tubes can extend out to the exterior of the said conduit and the said balloon, being located along the wall of the conduit and along the corresponding portion of the balloon; preferably, however, the balloon contains internally at least one perforated internal passage which communicates with said guide conduit, and at least one of said first and second guide tubes, and advantageously both of them, extends into the interior of the said conduit and then into the interior of said perforated internal passage.

The fact that the guide tubes extend into the interior of the balloon facilitates the insertion of the said lateral portions of the balloon in the respective branches of the pulmonary artery. The perforations of the said internal passage allow the inflation of the said balloon through the wall that delimits this internal passage.

The latter is preferably located at the centre of the cross section of the balloon. The said lateral portions of the balloon are thus centred on the guide wire when they are engaged on to the latter.

Preferably, the balloon has a circular cross section.

The balloon may be appropriately dimensioned, in cross section, in a manner such that its cross sectional surface area, in the inflated condition of the balloon, occupies 50% to 70% of the area of the cross section of the left branch or of the right branch of the pulmonary artery.

The said middle portion of the balloon, to which is connected the said conduit, can extend over approximately the central two thirds of the total length of the balloon, such that it may be possible for the said conduit to not be connected precisely in a central zone of the length of this balloon; however, this conduit is connected to the balloon in a central zone of the length of this balloon.

According to a first possibility, the balloon is placed in the aforementioned tubular sheath being folded at its middle portion, in a manner such that the two lateral portions thereof extend along and against one another.

Once the tubular sheath is in position within the trunk of the pulmonary artery, the device may be implanted by means of a procedure including the following steps:
- sliding movement of the two guide wires in relation to the balloon, so as to introduce these guide wires into the respective branches of the pulmonary artery;
- backward movement of the tubular sheath and/or pushing of the balloon out of the tubular sheath, so as to fully release the balloon;
- pushing of the balloon on to the two guide wires so as to introduce the lateral portions of the balloon into the respective branches of the pulmonary artery;
- implantation of the said port and introduction of the gas therein.

According to a second possibility, the balloon is placed lengthwise in the aforementioned tubular sheath, thus without median folding. In this case, once the tubular sheath is in position within the trunk of the pulmonary artery, the device is implanted by means of a procedure including the following steps:
- sliding movement of the guide wire corresponding to the lateral portion of the balloon that is nearest to the opening of the tubular sheath, so as to introduce this guide wire into one of the branches of the pulmonary artery;
- backward movement of the tubular sheath and/or pushing of the balloon out of the tubular sheath, so as to fully release the balloon;
- pushing of the deployed guide wire of the corresponding lateral portion of the balloon, so as to introduce this lateral portion into the corresponding branch of the pulmonary artery;
- sliding movement of the other guide wire so as to introduce this guide wire into the other branch of the pulmonary artery;
- pushing on this other guide wire of the corresponding lateral portion of the balloon, so as to introduce this lateral portion into the corresponding branch of the pulmonary artery;
- implantation of the said port and introduction of the gas therein.

The invention will be better understood and other characteristic features and advantages thereof will become apparent, upon reference be made to the accompanying schematic drawing, which shows, by way of a non-limiting example, a preferred embodiment of the device concerned.

DETAILED DESCRIPTION OF THE INVENTION

Figure 1:
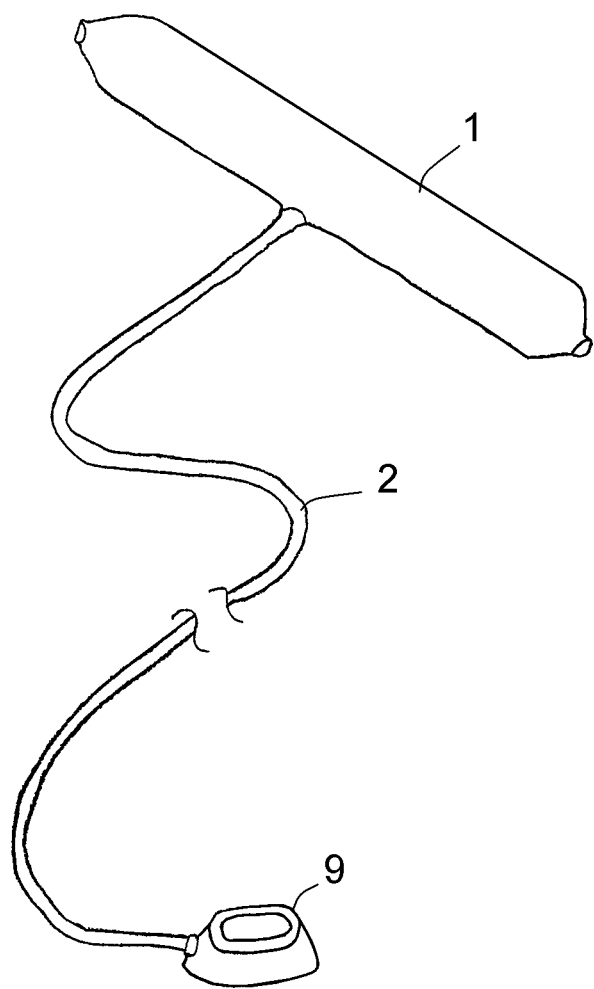
FIG. 1 is a view of the device.

FIG. 1 show an elongate inflatable balloon 1 in the inflated state, a conduit 2 connecting this balloon 1 to an implantable port 9.

Figure 2:
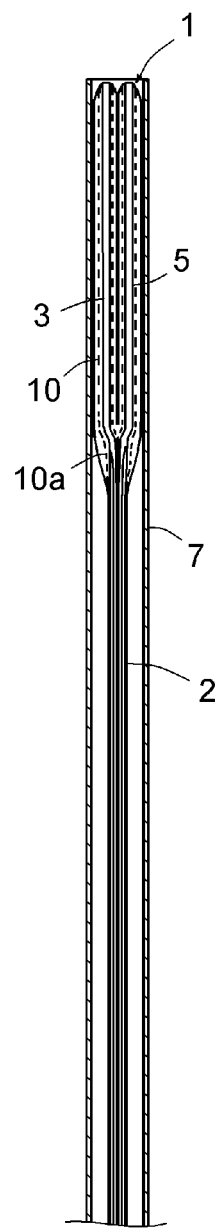
FIG. 2 is a view of constituent elements that form this device, in a folded state, accommodated within a tubular sheath.
Figure 3:
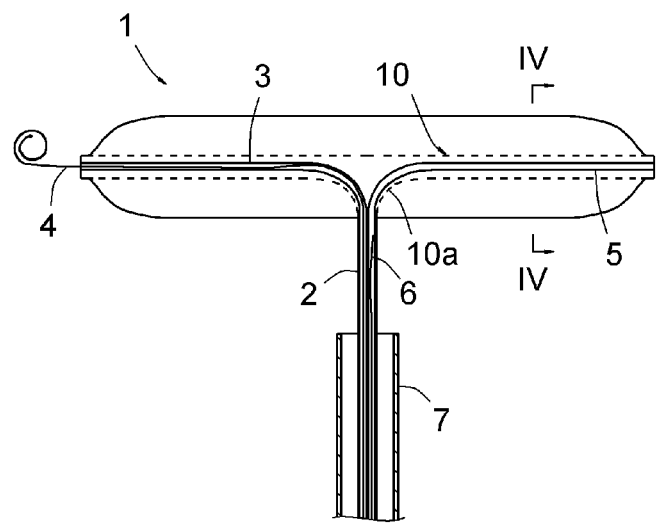
FIG. 3 is a view, in the unfolded state, of a balloon, of a part of a conduit and of a portion of a guide wire which is included in the device, these elements having been released from the said tubular sheath, by a backward movement of this tubular sheath, the said balloon being shown in an inflated state.
Figure 4:
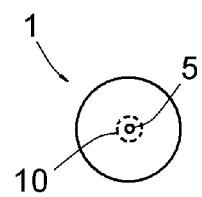
FIG. 4 is a sectional view of this balloon along the line IV-IV indicated in FIG. 3.

As shown in the FIGS. 2-4, the device also includes a first guide tube 3, a guide wire 4 capable of sliding in this tube 3, a second guide tube 5 and a guide wire 6 capable of sliding in this tube 5. This assembly constitutes a device for the treatment of pulmonary arterial hypertension. The balloon 1, in the deflated state, the conduit 2, the tubes 3 and 5 and the guide wires 4 and 6 are capable of being placed in a tubular sheath 7, as is shown in FIG. 2, this tubular sheath 7 forming a routing member for routing the device to its implantation site within the pulmonary artery, as shown in the FIGS. 5 to 7.

As shown in the FIGS. 3, 5, 8 and 9, the balloon 1 is elongate and is dimensioned so as to be extended in both the left branch G as well as the right branch D of the bifurcation B which is formed by the pulmonary artery AP. It has a circular cross section, the surface area of which, in the inflated state of the balloon, occupies, in a purely indicative manner, about 50%-70% of the area of the cross section of the left branch G or the right branch D.

The balloon 1 contains, at the centre thereof, a longitudinal internal tube 10, having a perforated wall, which opens in the longitudinal ends thereof and which have a central protrusion 10*a*. This protrusion has an end opening through which the tube 10 is connected to the conduit 2.

The envelope of the balloon 1 is connected in a sealed manner, in particular welded, to the longitudinal ends of the perforated internal tube 10 and to the conduit 2, such that this balloon 1 is adapted to be inflated by means of this conduit 2, through the perforations present on the tube 10.

The conduit 2, connected to the central protrusion 10*a*, is thus connected to the middle portion of the balloon 1 by one end. It is capable of being connected to the implantable port, in a sealed manner, by means of its other end.

This implantable port is of a well-known type, comprising of a body and a membrane which together define an empty space that forms the port itself. The membrane is intended to extend under the skin of the patient and can be pricked by means of the needle of a syringe in order to introduce the gas, in particular helium or $CO_2$, in the said empty space.

The guide tubes 3 and 5 extend within the conduit 2 and then, at the outlet of this conduit on the side of the balloon 1, one of them extends into the tube 10 all the way until it emerges opening out at one of the longitudinal ends of the balloon 1 (the tube 3 opens in the left end in FIG. 3) while the other tube extends into the tube 10 all the way until it emerges opening out at the other of the longitudinal ends of the balloon 1 (the tube 4 opens into the right end in FIG. 3).

The guide wires 4 and 6 are capable of sliding in the tubes 3 and 5 respectively, such that they can be deployed beyond the ends of the balloon 1 (wire 4 in FIG. 3) or retracted into the interior of the latter (wire 6 in FIG. 3). These guide wires 4, 6 are preformed so as to, when they are not constrained, form loops at their free ends in order to ensure that the wires do not to cause injury or perforation, according to a well-known technique.

Figure 6:
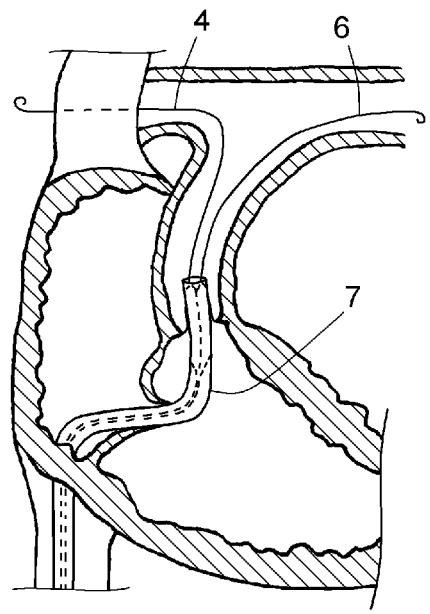
Figure 7:
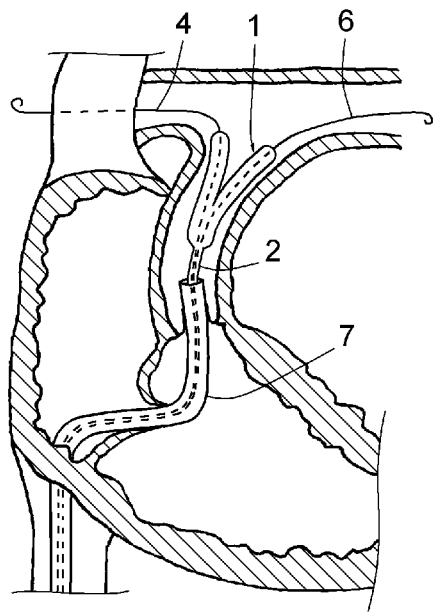
Figure 8:
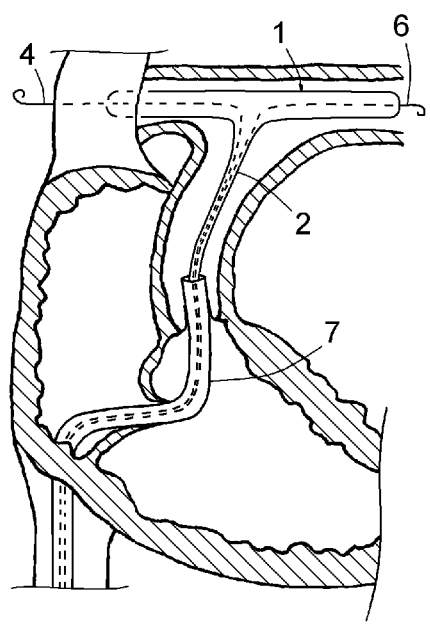

The tubular sheath 7 is of a known type, it is schematically represented by a single tube in FIGS. 2 and 3 in the interest of ensuring simplicity of representation, but in reality it has longitudinal wires sliding along the wall thereof, allowing, by pulling on one or more of them, the tubular sheath to bend so as to enable it to pass through tortuous body passageways, as is shown in FIGS. 6 to 8.

As shown in FIG. 2, the tubular sheath 7 is adapted to accommodate within its interior the balloon 1 in the deflated state, the conduit 2 and the guide tubes 3 and 5 containing the guide wires 4 and 6, and to release this balloon, this conduit and these guide tubes when it is retracted relative to these latter or when the balloon 1 is pushed out of it by means of a pusher (not shown) of known type.

In the embodiment shown in FIG. 2, the balloon 1 is placed in the tubular sheath 7 being folded at its middle portion, in a manner such that the two lateral portions thereof extend along and against one another.

Figure 5:
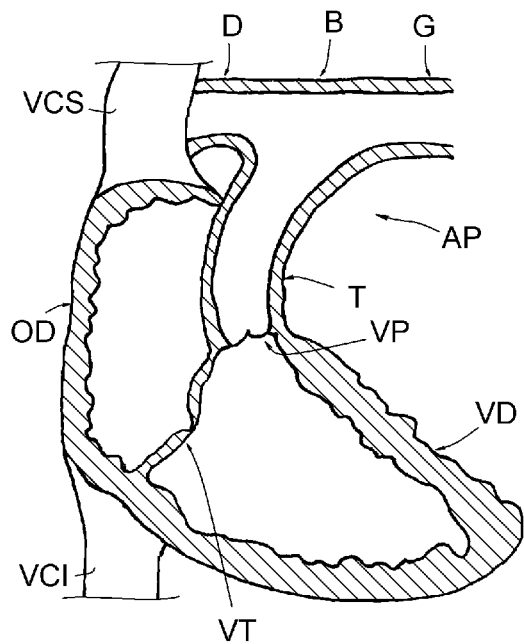
FIGS. 5 to 9 are sectional views of a right heart, over the course of multiple successive steps of implementation of the device, the heart being in diastole.

FIG. 5 shows a right heart in sectional view. Recognizable in the figure are the superior vena cava VCS, the right atrium OD, the inferior vena cava VCI, the tricuspid valve VT, the right ventricle VD, the pulmonary valve VP, the trunk T of the pulmonary artery AP and the left branch G and the right branch D of this artery, formed by the bifurcation B thereof.

The device previously described above is implanted in place by means of the following procedure.

The tubular sheath containing the balloon 1 in the deflated and folded state as previously described above is introduced into the inferior vena cava, through the tricuspid valve, into the right ventricle, through the pulmonary valve, right up to and into the trunk of the pulmonary artery, and then the guide wires 4 and 6 are deployed in the respective left and right branches, see FIG. 6.

The balloon 1 is then pushed out of the tubular sheath 7, by means of a sliding pusher (not shown) inserted into this tubular sheath, up to such point as it is fully released and free from the latter, which engages the lateral portions of the balloon 1 on to the guide wires 4 and 6, by sliding of the tubes 3 and 5 over these guide wires, see FIG. 7.

The push exerted on the balloon and/or on the conduit 2 is continued until such point as the said lateral portions of the balloon 1 are fully engaged in the respective branches G and D and the middle portion of the balloon extends in the bifurcation B, see FIG. 8.

Figure 9:
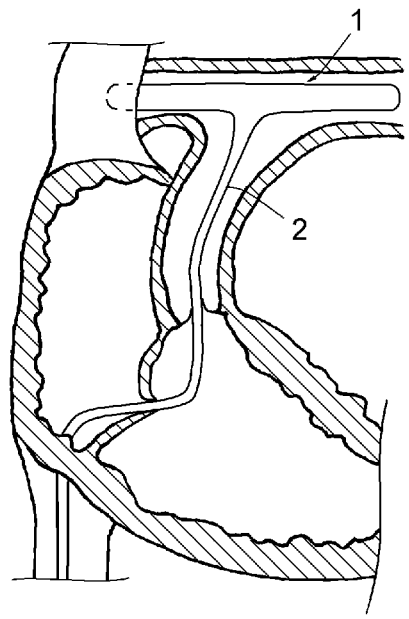

The guide wires 4 and 6 are then retracted and the tubular sheath 7 is removed, see FIG. 9.

Figure 10:
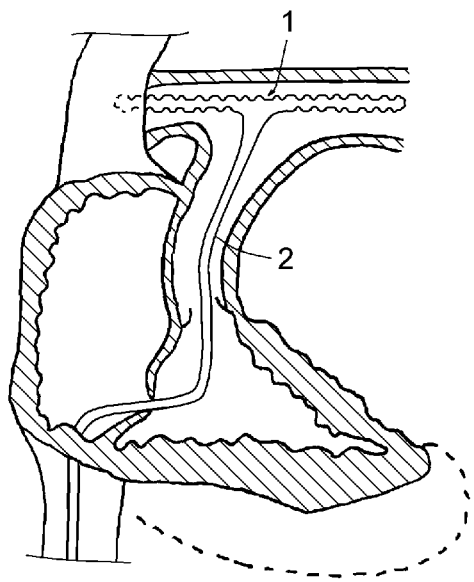
FIG. 10 is a view of the device similar to that in FIG. 9, while the heart is in systole.

The port is then implanted and connected in a sealed manner to the conduit 2, and then the gas is introduced in this port, in the conduit 2 and in the balloon 1. This introduction of gas is carried out at the pressure level that makes it possible for the balloon to be inflated during the right ventricular diastole, see FIG. 9, but for it to be compressed during the right ventricular systole, see FIG. 10, under the pressure which the flow of blood exerts on it, this compression temporarily generating an overpressure in the said implantable port and the said conduit 2.

The device according to the invention, so implanted, makes possible an increase in the diastolic pressure of the pulmonary artery, a decrease of the systolic pressure of the pulmonary artery, an increase of the arterial compliance and an immediate and sustained increase in the cardiac output, without the risk of mobility of the balloon 1. The latter is perfectly held in position by the engagement of its lateral portions in the said left and right branches and by the engagement of the conduit 2 in the trunk of the pulmonary artery.

Figure 11:
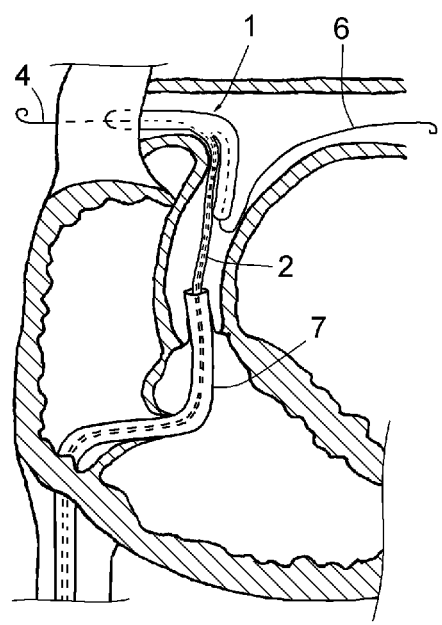
FIG. 11 is a view similar to that in FIG. 7 showing another mode for implanting of the device.

FIG. 11 shows a step of another procedure for implanting the device according to the invention in place, when, in accordance with a second possibility, the balloon 1 is placed lengthwise in the tubular sheath 7, therefore with no median fold.

In this case, once the tubular sheath 7 is in position in the trunk of the pulmonary artery, the following steps are implemented:

sliding movement of the guide wire corresponding to the lateral portion of the balloon that is nearest to the opening of the tubular sheath 7 (guide wire 4 as illustrated), so as to introduce the guide wire into one of the branches (right branch) of the pulmonary artery, backward movement of the tubular sheath 7 and/or pushing of the balloon 1 out of the tubular sheath 7 so as to fully release the balloon 1;

pushing of the deployed guide wire (4) of the corresponding lateral portion of the balloon 1, so as to introduce this lateral portion into the corresponding branch (D) of the pulmonary artery;

sliding movement the other wire guide (6) so as to introduce this wire guide (6) into the other branch (G) of the pulmonary artery;

pushing on this other guide wire (6) of the corresponding lateral portion of the balloon 1, so as to introduce this lateral portion into the corresponding branch (G) of the pulmonary artery;

implantation of the said port and introduction of the gas in the manner previously described above.

Figure 12:
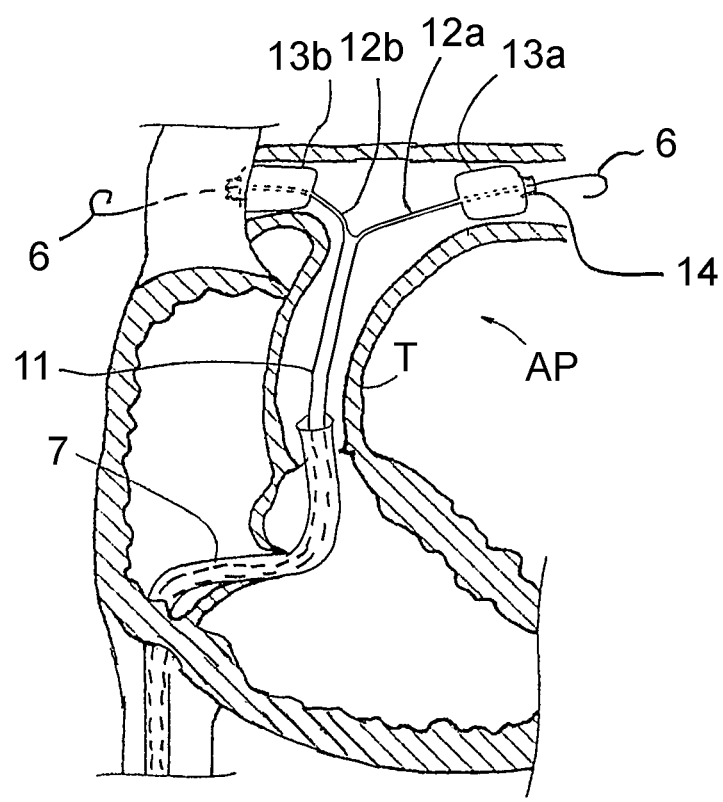
FIG. 12 is a view similar to that in FIG. 8 showing use of a bifurcated balloon catcher for implanting of the device.

FIG. 12 illustrates a further alternative embodiment where the balloon catheter structure comprises a bifurcated catheter body 11 having bifurcated branches 12a and 12b at its distal end. A right lateral balloon 13a is attached to the first branch 12a and a left lateral balloon 13b is attached to the second branch 12b. Each branch is configured to be delivered over a guide wire 6, and as with previous embodiments, the balloon catheter structure is configured to be advanced through a pre-placed tubular sheath 7. In preferred aspects, a radiopaque marker 14 may be located at the distal tip of each balloon 13a and 13b, and the balloons may each have diameters of approximately 20 mm and lengths of approximately 25 mm. The balloon 13a and 13b will preferably be connected to the port 9 (FIG. 1) through a single lumen running through the proximal portion of catheter body 11. The use of the bifurcated balloon catheter 11 may have advantages in deployment. In particular, in many instances, it may be easier to deflate separate balloon segments than to deflate the single, larger T-shaped balloon structure of the prior embodiments.

In still further alternative embodiments of the methods herein, separate catheters and/or separate ports can be used to place the individual balloon segments in the right and left branches of the pulmonary artery, but in general such approaches will be less preferred.

The invention thus provides a device for the treatment of pulmonary arterial hypertension further presenting the aforementioned key advantages as compared to similar devices of the prior art.

This invention has been described here above with reference to embodiments provided purely by way of example. It is obvious that it is not limited to these embodiments but extends to all the embodiments described and covered by the appended claims.

The invention claimed is:

1. A system for treating pulmonary hypertension, said system comprising:
    an implantable port configured for subcutaneous implantation and having an internal chamber;
    a guide conduit structure attached at one end to the implantable port; and
    a single inflatable balloon structure attached to another end of the guide conduit structure having a first lateral balloon segment, a second lateral balloon segment, and a central zone between the first and second lateral balloon segments, wherein the balloon structure is configured so that when the guide conduit structure is positioned in a pulmonary artery the first lateral balloon segment will occupy a left branch of the pulmonary artery and the second lateral balloon segment will occupy a right branch of the pulmonary artery, wherein the guide conduit structure includes first and second guide tubes, wherein the first guide tube provides a first guide wire path along or through the guide conduit structure and the first lateral balloon segment and the second guide tube provides a second guide wire path separate from the first guide wire path along or through the guide conduit structure and the second lateral balloon segment; wherein a distal end of the guide conduit structure forms a T-junction located in the central zone of said single balloon between said first lateral balloon segment and said second lateral balloon segment and wherein the first guide tube extends from a first branch of the T-junction and the second guide tube extends from a second branch of the T-junction.

2. A system as in claim 1, wherein the implantable port is configured to receive a needle which is transcutaneously advanced to deliver a balloon inflation medium.

3. A system as in claim 1, wherein
    the first guide tube passes along the first lateral balloon segment to provide a guide wire path along the first lateral balloon segment and the second guide tube passes along the second lateral balloon segment to provide a guide wire path along this second lateral balloon segment.

4. A system as in claim 1, wherein
    the first guide tube passes through the first lateral balloon segment to provide a guide wire path therethrough and the second guide tube passes through the second lateral balloon segment to provide a guide wire path therethrough.

5. A system as in claim 1, wherein said single balloon contains internally at least one perforated internal passage which communicates with said guide conduit structure, and wherein at least one of said first and second guide tubes extends into the interior of the guide conduit structure and then into the interior of said perforated internal passage.

6. A system as in claim 5, wherein said at least one perforated internal passage is located at the center of the cross section of said single balloon.

7. A system as in claim 6, wherein said single balloon has a circular cross section.

8. A system as in claim 5, wherein the perforated internal passage has a central protrusion connected to the guide conduit structure, a first branch extending from the protrusion through the first branch of the balloon, and a second branch extending from the protrusion through the second branch of the balloon, wherein the first guide tube extends through the protrusion and the first branch of the perforated internal passage and the second branch extends through the protrusion and the second branch of the perforated internal passage.

9. A system as in claim 1, wherein each segment of the balloon structure is selected to occupy 50% to 70% of the area of the cross section of the left branch or of the right branch of the pulmonary artery of a patient to be treated.

10. A system as in claim 1, further comprising a sheath configured to constrain the inflatable balloon structure for delivery to a base of the pulmonary artery and to allow advancement of the first and second lateral balloon segments through the pulmonary artery into the left and right branches of the pulmonary artery, respectively.

11. A system as in claim 10, wherein the balloon segments of the inflatable balloon structure are configured to lie in a side-by-side configuration when constrained by the sheath.

12. A system as in claim 10, wherein the inflatable balloon structure is configured so that the first and second lateral segments lie along a common axis in parallel to an axis of the guide conduit structure when constrained by the sheath.

* * * * *